United States Patent [19]

Reddel et al.

[11] Patent Number: 5,443,954

[45] Date of Patent: * Aug. 22, 1995

[54] IMMORTALIZED NON-TUMORIGENIC HUMAN BRONCHIAL EPITHELIAL CELL LINES

[75] Inventors: Roger R. Reddel, Camperdown, Australia; Yang Ke, Beijing, China; Johng S. Rhim, Bethesda, Md.; Douglas E. Brash, New Haven, Conn.; Robert T. Su, Lawrence, Kans.; John F. Lechner, Bethesda, Md.; Brenda I. Gerwin, Bethesda, Md.; Curtis C. Harris, Bethesda, Md.; Paul Amstad, Epolinges, Switzerland

[73] Assignee: The United States of America as represented by the Department of Health and Human Services, Washington, D.C.

[ * ] Notice: The portion of the term of this patent subsequent to Dec. 5, 2006 has been disclaimed.

[21] Appl. No.: 636,712

[22] Filed: Jan. 2, 1991

Related U.S. Application Data

[63] Continuation-in-part of Ser. No. 265,883, Nov. 1, 1988, abandoned, which is a continuation-in-part of Ser. No. 114,508, Oct. 30, 1987, Pat. No. 4,885,238.

[51] Int. Cl.$^6$ .................. C12Q 1/02; C12N 5/10
[52] U.S. Cl. .................. 435/7.21; 435/240.2
[58] Field of Search .......... 435/29, 170, 5, 30, 435/32, 240.1, 240.2, 172.1, 7.2, 7.21; 935/52, 57

[56] References Cited

U.S. PATENT DOCUMENTS

| | | | |
|---|---|---|---|
| 4,816,395 | 3/1989 | Hancock | 435/29 |
| 4,885,238 | 12/1989 | Reddel et al. | 435/29 |
| 4,980,290 | 12/1990 | Reznikoff et al. | 435/240.2 |

OTHER PUBLICATIONS

Reddel et al., *Cancer Research*, vol. 48, 1988, pp. 1904–1909.
Baker et al., *Science*, vol. 249, 1990, pp. 912–914.
Sasajima et al, *JNCI*, vol. 78, No. 3, pp. 419–423.
Lechner et al, *J Tissue Culture Methods*, vol. 9, No. 2, 1989, pp. 43–48.
Reddel, et al *Oncogene Research*, 1988, vol. 3, pp. 401–408.
Amstad, et al, *Molecular Carcinogenesis*, 1:151–160 (1988).
Reddel, et al *Journal of the National Cancer Institute*, 81, No. 12, Jun. 21, 1989.
Ura et al, *Cancer Research*, 49, pp. 4615–4621, Aug. 15, 1989.
Pfeifer, et al, *Proc. Natl. Acad. Sci, USA*, 86, pp. 10075–10079 Dec. 1989.
Bonfil, et al, *Journal of the National Cancer Institute*, 81, No. 8, Apr. 19, 1989.
Lechner, et al, *Cancer Research*, 43, Dec. 1983, pp. 5915–5921.
Yoakum, et al, *Science*, 227, Mar. 1985, pp. 1174–1179.
Brash et al, *Molecular and Cellular Biology*, 7, 1987, pp. 2031–2034.
Nakagawa, et al. *Federation Proceedings*, 1987, 46, p. 718.
Lechner et al, *Proceedings of the American Association for Cancer Research*, 28, 1987, p. 60, Abstract No. 240.

*Primary Examiner*—Richard A. Schwartz
*Assistant Examiner*—James Ketter
*Attorney, Agent, or Firm*—Townsend and Townsend Khourie and Crew

[57] ABSTRACT

Immortalized human bronchial epithelial and human mesothelial cell lines have been obtained. Various uses of these cell lines have been described.

19 Claims, 1 Drawing Sheet

IMMORTALIZED NON-TUMORIGENIC HUMAN BRONCHIAL EPITHELIAL CELL LINES

CROSS-REFERENCE TO RELATED APPLICATIONS

This application is a Continuation-In-Part application of Ser. No. 07/265,883, filed on Nov. 1, 1988, now abandoned, which is a Continuation-in-Part application of Ser. No. 07/114,508, filed on Oct. 30, 1987, now U.S. Pat. No. 4,885,238, which are herein incorporated by reference.

BACKGROUND OF THE INVENTION

1. Field of the Invention

The present invention relates to immortalized cell lines. More particularly, the present invention relates to immortalized human lung cell lines or cell lines derived therefrom.

2. Description of the Related Art

Lung cancer is one of the more common forms of cancer and the cell type in which the majority of these cancers arise is the bronchial epithelial cells. Mesothelial cells are a less common, but important, site of origin of lung cancer. Both normal human bronchial and mesothelial cells could be cultured in vitro, but only for a limited period of time before cellular replication ceases. When transformed by transfection of the viral Harvey ras oncogene (Yoakum, et al., *Science*, 227:1174, 1985), human bronchial epithelial cells replicate for longer periods of time, but these cells are tumorigenic, grow in serum-containing media as do carcinoma cell lines, and have been constructed to contain an oncogene closely related to oncogenes sometimes found in human carcinomes. Similarly, human bronchial carcinoma and mesothelioma cell lines are tumorigenic.

SUMMARY OF INVENTION

An object of this invention is to provide both tumorigenic and non-tumorigenic human cell lines of bronchial and mesothelial epithelial cell origin with unlimited proliferative potential and capable of growing in the same serum-free media as their normal counterpart cells, and which do not contain an oncogene found in naturally occurring tumors.

DETAILED DESCRIPTION OF INVENTION

Figure 1:
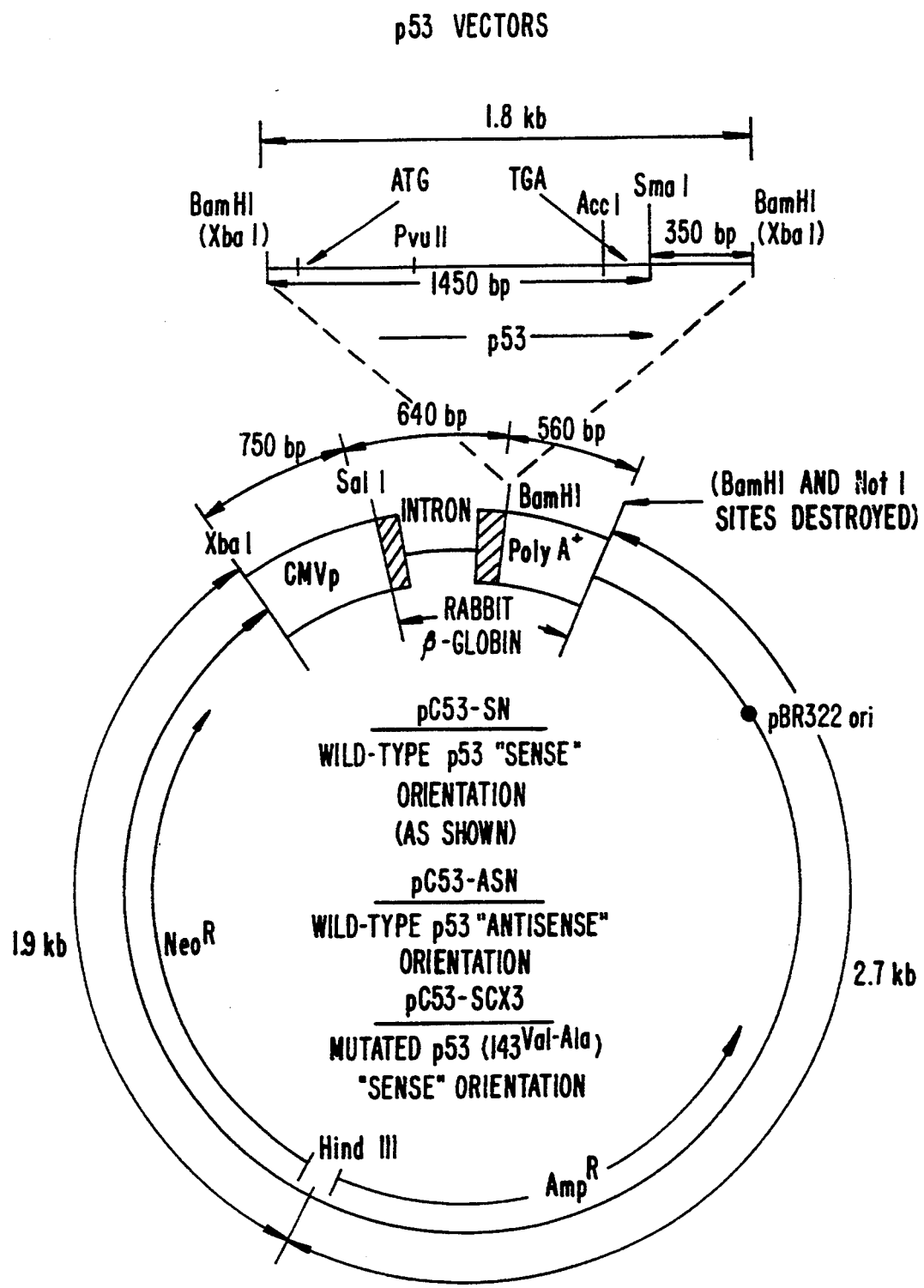
FIGURE 1 shows p53 vectors.

The above and other objects and advantages of the present invention are achieved by both a tumorigenic and a non-tumorigenic, human lung epithelial cell line continually growing when cultured in vitro in suitable growth medium.

The description of their development is similar to that for the BET-1A and the BET-2A cell lines as described in the U.S. patent application Ser. No. 07/114,508, filed on Oct. 30, 1987.

The term "immortalized" as used herein means that the cell line grows continually without senescence when cultured in vitro in a suitable growth medium.

General Method for Construction of Cell Lines

Cell lines were derived from cell lines which are the subject of the U.S. application Ser. No. 07/114,508, either by subcloning these cell lines to obtain sublines with desired properties, or by transferring oncogenes into these cell lines. Subcloning was by the limiting dilution method. Oncogene transfer into these cell lines was performed either by transfection of plasmid DNA or by retroviral infection. The transfected DNA plasmid either contained a selectable marker gene or were co-transfected with a plasmid containing a selectable marker, and in some cases the retroviral vector contained a selectable marker gene. Where a selectable marker was transferred into the cells along with the oncogene in any of these ways, the cell populations were enriched for oncogene-containing cells by selecting for the selectable marker. Where a selectable marker was not transferred in one of these ways, the cell population was enriched for oncogene-containing cells by injecting them subcutaneously into athymic nude mice and then establishing a tumor cell line from a tumor formed by this inoculum. One cell line was also derived by injecting athymic nude mice subcutaneously with a cell population pre-enriched by selecting for a selectable marker then establishing a tumor cell line from a tumor formed by this inoculum.

Normal human bronchial epithelial (NHBE) cells were cultured from explants of autopsy specimens from three noncancerous individuals. The cells were cultured in a serum-free medium, LHC-9, harvested by trypsinization and seeded in 10 ml growth medium into 100 mm culture dishes whose growth surfaces had been coated with a solution of bovine serum albumin, fibronectin and collagen as described by Lechner, et al., *J. Tissue Culture Methods* 9:43–48, 1985. Normal human mesothelial (NHM) cells were cultured from pleural effusions or ascite fluids as described by Lechner, et al, (*Proc. Natl. Acad. Sci. USA* 82:3884–3888, 1985). The cells were infected with SV40 virus or with adenovirus-12 SV40 hybrid virus, or transfected with a recombinant plasmid pRSV-T (obtained from the National Cancer Institute), which is an SV40 ori-construct containing the SV40 early region genes and the Rouse sarcoma virus long terminal repeat. Transfection was by strontium phosphate DNA coprecipitation as described by Brash et al., *Molec. Cell. Biol.* 7:2031–2034, 1987. Esophageal cells were transfected with 10 ug DNA precipitated at pH 7.30. The cells were exposed to the precipitate for 4 hours before shock with 15% glycerol for 30 seconds (Brash et al., supra). The cells were cultured in LHC-9 medium and were passaged continuously whenever they reached subconfluence. The cells were passaged approximately 10 times before the cultures senesced. After variable periods of time, colonies of dividing cells appeared from which cell lines have been established with apparently unlimited proliferative potential.

Colonies of cells transformed by each of these three methods were easily recognizable morphologically using phase contrast microscopy and were individually trypsinized and serially passaged. In all cases the lifespan of these cultures was extended compared to NHBE or NHM; most of the cultures underwent a prolonged period of senescence referred to as "crisis". With continued culture, in some cases colonies of cells which had escaped senescence arose. Such surviving colonies were subsequently passaged for extended periods of time and showed unlimited growth potential. Like NEBE cells, but unlike bronchial carcinoma cells, some of the cell lines thus derived retained the capacity to undergo squamous differentiation in response to serum exposure. Injection of these cells into irradiated athymic nude mice did not result in formation of tumors after periods of up to nine months. Furthermore, these cell lines were found to be suitable recipients for transfection of additional oncogenes and useful for testing the cytotoxicity potential of chemical and physical agents, the growth inhibition or promoting capability of biological agents, and squamous differentiating potential of chemical and biological agents.

Human lung cell lines 1–8 were deposited at the American Type Cell Culture (ATCC), Rockville, Md., on Oct. 17, 1988, cell line 9 was deposited with the ATCC on Dec. 31, 1990, cell line 10 was deposited with the ATCC on Dec. 28, 1990, and cell lines 12 and 13 were deposited with the ATCC on Oct. 27, 1992. All deposits are in accordance with the Budapest Treaty. The cell lines are:

1. BVK Tll: BEAS 2B cell neoplastically transformed by transfected vKi-ras oncogene (ATCC CRL 9871);
2. BEAS 2B/EJ-ras: BEAS-2B cell neoplastically transformed by transfected EJ-ras oncogene (ATCC CRL 9866);
3. BEAS 2B/N-ras: BEAS-2B cell neoplastically transformed by transfected N-ras (ATCC CRL 9870);
4. BEAS 2B-S6: Subclone of BEAS-2B cells (ATCC CRL 9867);
5. BEAS 2B-c-myc: BEAS 2B cell transfected with c-myc (ATCC CRL 9869);
6. BEAS 2B-c-raf-1: BEAS-2B cell transfected with c-raf-1 (ATCC CRL 9864);
7. RMT-1: BEAS 2B cell neoplastically transformed by transfected c-myc and c-raf-1 oncogenes (ATCC CRL 9868);
8. MET 5A/EJ-ras: Human mesothelial cell line MET5A neoplastically transformed by transfected EJ -ras oncogene (ATCC CRL 9865);
9. BERB: BEAS-2B transfected with pLTRNeoERB (ATCC CRL 10635);
10. BERB (subclone 2): BEAS-2B transfected with pLTRNeoERB (ATCC CRL 10634);
12. Bp53WT: BEAS-2B cell line transfected with pC53-SN (ATCC CRL 11168); and
13. Bp53MT143: BEAS-2B cell line transfected with pC53-SCX3 (ATCC CRL 11169).

All the deposits shall be viably maintained and replaced if they became non-viable for a period of 30 years from the date of the deposit, or for 5 years from the last date of request or a sample of the deposit, whichever is longer, and made available to the public without restriction in accordance with the provisions of the law. The Commissioner of Patents and Trademarks, upon request, shall have access to the deposit.

EXAMPLE 1

Development of BVK-Tll Cell Line

BEAS-2B cells, passage 57, were infected with Kirsten sarcoma virus pseudotyped with baboon endogenous virus, by exposing the cells to the virus at $10^4$ focus forming units/ml for 4 hours at 37° C. The cells were incubated in LHC-9 medium until confluent, then subcultured to obtain sufficient cells for injection into athymic nude mice irradiated 24 hours previously with 350 rad. Mice were injected with $5 \times 10^6$ cells subcutaneously. Tumors arising from these inoculum were individually established as cell lines by mincing the tumor tissue and culturing it in LHC-9 medium. Cells that grew out from the tumor pieces onto the culture dish were subcultured as a cell line. One such cell line was designated BVK-Tll, and has been shown by Western analysis to contain the viral Kirsten ras oncogene.

EXAMPLE 2

Development of the BEAS-2B/EJ-ras Cell Line

BEAS-2B cells, passage 52, were transfected via strontium phosphate co-precipitation (Brash et al., vide supra) with a recombinant plasmid containing the human c-Ha-ras oncogene mutated so that codon 12 encodes valine. The plasmid was obtained from NCI and consists of pSV2neo (Southern et al., vide supra) joined at the BamHl site to the 6.6 Kb BamHl DNA fragment encoding the mutant o-Ha-ras oncogene from the EJ human bladder carcinoma cell line. BEAS-2B cells transfected with this plasmid were subcultured and selected in LHC-9 medium for resistance to the antibiotic G418 (Geneticin). G418-resistant cells were then subcultured until they were sufficient for cryopreservation and injection into athymic nude mice. These cells were designated BEAS-2B/EJ-ras and have been shown to be tumorigenic in nude mice and have been shown by Western analysis to express the codon 12 valine mutant ras p21 protein.

EXAMPLE 3

Development of the BEAS-2B/N-ras Cell Line

BEAS-2B cells, passage 52, were transfected via strontium phosphate co-precipitation (Brash et al., vide supra) with a recombinant plasmid containing the human N-ras gene mutated so that the 12th codon encodes aspartate. The plasmid was obtained from Dr. Channing Der and was constructed by recombining the pZipNeoSV(X) retrovirus (Cepko et al., vide supra) at its unique BamHl restriction endonuclease site with a 1.1 kB DNA fragment encoding the mutant N-ras oncogene. Following transfection of this DNA into BEAS-2B cells, G418-resistant cells were selected (Southern et al., vide supra) and serially subcultured; the cell line so derived was designated BEAS-2B/N-ras. This cell line is tumorigenic when injected subcutaneously in athymic nude mice, and has been shown by Western analysis to express the codon 12 aspartate mutant ras p21 protein.

EXAMPLE 4

Development of the BET-2A Cell Line

NHBE cells were cultured from explants of autopsy specimens from noncancerous individuals as described previously hereinabove. The cells were cultured in a serum-free medium, LHC-9, harvested by trypsinization and seeded in 10 ml growth medium into 100 mm culture dishes (Lux, Miles Scientific, Naperville, Ill.) whose growth surfaces had been coated with a solution of bovine serum albumin, fibronectin and collagen (Lechner, et al., 1985, supra).

The cells were transfected with a plasmid, pRSV-T, (obtained from National Cancer Institute) which is an SV40 ori- construct containing the SV40 early region genes and the Rous sarcoma virus long terminal repeat (LTR).

Transfection was by DNA strontium phosphate co-precipitation as described previously (Brash, et al., supra). $5 \times 10^5$ NHEE cells plated in 100 mm dishes were transfected with 10 ug DNA precipitated at pH 7.8. The cells were exposed to the precipitate for 4 hr before glycerol shock (Brash, et al., supra). Three days after transfection the cells were passaged. Thereafter, the cell culture medium was changed twice weekly. Three transformed colonies were subcultured individually at 28 days following transfection, and the clonal cell strains thus derived continued to proliferate in culture for 11 weeks after which time the cultures senesced (i.e., entered "crisis"). After a further 36 weeks, colonies of dividing cells appeared in culture BET-2A from which a cell line has become established; BET-2A cells have been in culture for more than a year from the time of initial transfection. The BET-2A cell line, like the BES-1A1.6 cell line, appears to be resistant to the squamous differentiation-inducing effects of serum. Whereas NHBE cells are able to be induced to undergo squamous differentiation when exposed to serum, bronchial carcinomas are resistant to this effect (Lechner, et al., *Cancer Res.*, 43:5915–5921, 1983). TBE cell lines (human bronchial epithelial cells transformed by the v-Ha-ras oncogene) are tumorigenic and are resistant to this effect of serum. The non-tumorigenic BET-2A cell line is, therefore, intermediate between normal and fully malignant bronchial epithelial cells in this respect.

EXAMPLE 5

Development of MeT-5A Cell Line

Human mesothelial cells were cultured as described by Lechner, et al., *Proc. Natl. Acad. Sci. USA*, 82: 3884–3888, 1985, and were transformed at a frequency of $2 \times 10^{-4}$ by transfection using strontium phosphate coprecipitation (Brash, et al., supra) of a recombinant plasmid, pRSV-T, containing the SV40 virus early region. Colonies of cells transformed by the plasmid, pRSV-T, were isolated and propagated by serial passaging for periods of up to 140 days and 60–70 population doublings from the time of transfection, before cellular senescence occurred. This contrasts with the usual culture lifespan of normal mesothelial cells of 30 days and 15 population doublings. Colonies of dividing cells arose from one such senescent culture, and from these colonies an immortalized cell line, MeT-5A, has been established by continued passaging. This cell line is non-tumorigenic. Although it has been maintained routinely in the serum-containing LHC-MM medium, it also grows well in a serum-free medium.

EXAMPLE 6

Development of BBM Cell Line

BEAS-2B cells were transfected via strontium phosphate coprecipitation (Brash, et al., *Molec. Cell Biol.*, 7:2031–2034, 1987) with a recombinant plasmid, B-mys/pSV2neo, which had been constructed by ligating a BanH1/EcoR1 fragment of the c-myc gene from the Burkitt's lymphoma cell line CA46 (Showe, et al., *Mol. Cell Biol.* 5:501–509, 1985) to a BamH1/EcoR1 fragment of the pSV2neo vector (Southern, et al., *Mol. Appl. Genet.*, 1:327–341, 1982). BEAS-2B cells so transfected were selected in LCH-9 medium with G418 (Geneticin), and colonies resistant to G418 were isolated individually and subcultured. The cell line arising from one such colony has been designated BBM.

EXAMPLE 7

Development of BZR Cell Line

This cell line has been derived by infecting the BEAS-2B cell line with a recombinant containing the viral Harvey-ras (v-Ha-ras) oncogene. The cell line so derived is highly tumorigenic in athymic nude mice.

The details of the construction are as follows. Zipneo-v-Ha-ras recombinant retrovirus was constructed by recombining the pZipNeoSV(X) retrovirus (Cepko, et al., *Cell*, 37:1053–1062, 1984) at its unique Bam H1 restriction enzyme site with a Bam H1-linked 1.3 Kb fragment of the Hi clone (Ellis, et al., *J. Virol.*, 36:408–420, 1980) containing the v-Ha-ras oncogene. Recombinant DNA molecules containing the v-Ha-ras DNA in sense orientation with respect to the pZip-NeoSV(X) retrovirus 5' long terminal repeat, were identified by standard DNA manipulation techniques and were used to transfect the psi2 packaging mutant cell line (Mann, et al., *Cell*, 33:153–159, 1983). Supernatants from these cells were shown to contain infectious retrovirus, and were used to infect the amphotrophic packaging mutant cell line, psiAM (Cone, et al., *Proc. Natl. Acad. Sci. USA*, 81:6349-6353, 1984). Supernatants from this cell line were titered and used to infect BEAS-2B cells.

Following infection of BEAS-2B cells with this virus, G418 resistant cells were selected (Southern, et al., *J. Mol. Appln. Genet.*, 1:327-341, 1982) and serially subcultured; the cell line so derived was designated BZR. This cell line is highly tumorigenic, forming tumors with a latency period of 2 weeks in 12/15 athymic nude mice each injected with $5 \times 10^6$ cells subcutaneously.

A deposit of the cell lines of the present invention has been made at the ATCC, Rockville, Md., on Jun. 12, 1987 and Jul. 14, 1987 under the accession numbers CRL 9608, 9609, 9442, 9443, 9444, 9482 and 9483, corresponding to cell lines BES-1A1-6, BEAS-2B, BET-1A, BET-2A, MeT-5A, BBM and BZR, respectively.

EXAMPLE 8

Development of MET-5A/EJ-ras Cell Line

MeT-5A cells, passage 71, were transfected via strontium phosphate coprecipitation (Brash et al., vide supra) with a recombinant-plasmid containing the human c-Ha-ras oncogene mutated so that codon 12 encodes valine. The plasmid was obtained from NCI and consists of pSV2neo joined at the BamHI site to the 6.6 Kb BamHI DNA fragment encoding the mutant c-Ha-ras oncogene from the EJ human bladder carcinoma cell line. Met-5A cells transfected with this plasmid were subcultured until they were sufficient for cryopreservation and injection into athymic nude mice. These cells were designated MeT-5A/EJ-ras and have been shown to be tumorigenic in nude mice and have been shown by Western analysis to express the codon 12 valine mutant ras p21 protein.

EXAMPLES 9-11

Development of BERB Cell Line and Subclones 2 and 6

The BERB cell line has been derived by transfecting, using the strontium phosphate method (Brash, et al., *Molec. Cell Biol.*, 7:2031–2034, 1987), the BEAS-2B cell line with a recombinant (pLTRNeoERB) containing erb-B2 gene, which is also called HER-2 and neu, and selecting colonies resistant to G418 (Geneticin) in LHC-9 medium containing G418. Subcloning of the transfected cells was performed by the limiting dilution technique and subclones 2 and 6 were selected by enzyme immunocytochemistry for high expression of erb-B2. Subclone 2 has a spindle cell morphology and a colony forming efficiency of $38 \pm 12\%$ (mean ± standard deviation) whereas subclone 6 has a polygonal morphology and has a colony forming efficiency of 96±7%. The BERB cell line and its subclones 2 and 6 have been injected into athymic nude mice to determine their tumorigenic potential. These cell lines are weakly tumorigenic.

EXAMPLES 12-13

Development of Bp53WT and Bp53MT143 Cell Lines

Bp53WT and Bp53MT143 cells lines have been derived by transfecting BEAS-2B cell line with recombinants (pC53-SN or pC53-SCX3; Baker et al, *Science* 249:912-915, 1990), that contain the coding sequences of the wild-type p53 gene or mutant (143 $^{Val \rightarrow ala}$) p53 gene, respectively, and selecting colonies resistant to G418 (Geneticin) in LHC-9 medium containing G418. The colony forming efficiencies of Bp53WT and Bp53MT143 were 18±4% (mean ± standard deviation) and 26±2%, respectively. Expression of transfected p53 genes was shown by the RNAase protection technique. The tumorigenic potential of Bp53WT and Bp53MT143 cell lines is being determined by injecting $5 \times 10^6$ cells of each line subcutaneously into athymic nude mice.

UTILITY OF CELL LINES (1) Identification of potential chemotherapeutic drugs: These cells are useful for screening chemicals suitable for the treatment of cancer and related diseases, by growing them in vitro in medium containing the chemical to be tested and then, after a suitable period of exposure, determining whether and to what extent cytotoxicity has occurred, e.g., by trypan blue exclusion assay or related assays (Paterson, *Methods Enzymol.*, 58:141, 1979), or by growth assays such as colony forming efficiency (MacDonald, et al., *Exp. Cell. Res.*, 50: 417, 1968), all of which are standard techniques well known in the art. Bp53WT and Bp53MT143 may be especially useful for identifying chemotherapeutic drugs that will mimic and/or enhance the action of tumor suppressor genes.

(2) Studies of the control of squamous differentiation, and identification of chemical and biological agents which induce squamous differentiation: This is accomplished by assays previously described for normal human bronchial epithelial cells (Masui, *Proc. Natl. Acad. Sci. USA*, 83:2438, 1986). As noted in the cell line specification, some retain ability to undergo squamous differentiation in response to serum. Induction of terminal differentiation can be an effective way of controlling the growth of cancer. Chemical and biological substances are screened for their ability to induce differentiation by adding them to the growth medium of these cells and then after a suitable time interval determining whether a complex of changes including cessation of DNA synthesis and the appearance of squamous morphology has occurred. The cells are also useful for studies of the biological mechanisms of squamous differentiation, and the existence of both serum-resistant and serum-sensitive cell lines enables comparisons and identification of genes of their protein products involved in the process of differentiation.

(3) Studies of metabolism of carcinogens and other xenobiotics: Carcinogens and other xenobiotics can be added to the growth medium of these cells and then the appearance of metabolic products of these compounds can be monitored by techniques such as thin layer chromatography or high performance liquid chromatography and the like, and the interaction of the compounds and/or their metabolites with DNA is determined.

(4) Studies of DNA mutagenesis: Substances known or suspected to be mutagens can be added to the growth medium of the cells and then mutations can be assayed, e.g., by detection of the appearance of drug resistant mutant cell colonies (Thompson, *Methods Enzymol.*, 58:308, 1979). Similarly, cell-mediated DNA mutagenesis may occur by cocultivating the cells with cell types known or suspected to be capable of secreting mutagenic compounds (Hsu, et al., *Proc. Natl. Acad. Sci. USA*, 75:2003, 1978).

(5) Studies of chromosome damaging agents: Substances known or suspected to cause chromosomal damage can be added to the culture medium of these cell lines, and then the extent of chromosomal damage can be measured by techniques such as measurement of the frequency of sister chromatid exchange (Latt, et al., In: Tice, R. R. and Hollaender, A., *Sister Chromatid Exchanges*. New York: Plenum Press, pp. 11 ff., 1984).

(6) Studies of malignant transformation by chemical, physical and viral agents, and transferred genes including oncogenes and high molecular weight genomic DNA from tumors, using standard assays such as anchorage independent growth or tumor formation in athymic nude mice. For example, a cloned cellular oncogene from a human tumor has been transferred into the BEAS-2B cell line; the cell line thus derived is BBM. This cell line has been shown to be resistant to the squamous differentiation inducing effects of serum. In a second example, a cloned viral oncogene, v-Ha-ras, has been introduced into the BEAS-2B cell line. The cell line thus derived is BZR as discussed in the parent application. This cell line has been shown to be able to form tumors in nude mice with a latency period of two weeks, and is able to grow in an anchorage-independent fashion in soft agar.

(7) Use of cells altered by transfer of oncogenes as in paragraph 6 above to screen for potential chemotherapeutic agents (by the techniques described in paragraph 1 above) especially those which can be specific for cells transformed by the activation of particular oncogenes or combination of oncogenes.

(8) Studies of cellular biochemistry, including changes in intracellular pH and calcium levels, as correlated with cell growth and action of exogenous agents including but not limited to those described in paragraphs 1 through 7 above. To study intracellular pH and calcium levels, cells in suitable culture vessels are exposed to fluorescent indicator dyes and then fluorescence emissions are detected with a fluorescence spectrophotometer (Grynkiewicz, et al., *J. Biol. Chem.*, 260:3440-3450, 1985).

(9) Studies of cellular responses to growth factors and production of growth factors: Identification and purification of growth factors important for growth and differentiation of human bronchial epithelial cells. These cells are particularly useful for such an application since they grow in serum-free media. Therefore, responses to growth factors can be studied in precisely defined growth media and any factors produced by the cells can be identified and purified without the complication of the presence of serum.

(10) Use of recombinant DNA expression vectors to produce proteins of interest. For example, the gene encoding a protein of therapeutic value can be recombined with controlling DNA segments (i.e., containing a promoter with or without an enhancer sequence), transferred into the cell (e.g., by strontium phosphate transfection) and then the protein produced can be harvested from the culture supernatant or a cellular extract by routine procedures well known in the art.

(11) Studies of intracellular communication e.g., by dye scrape loading assays. To determine whether the cells growing in vitro have the ability to communicate via gap junctions, the cultures can be scraped, e.g., with a scalpel, in the presence of a fluorescent dye in the growth-medium. Cells at the edge of the wound are mechanically disrupted and therefore take up dye; whether intercellular communication has occurred can be ascertained by determining whether cells distant from the wound also contain dye.

(12) Characterization of cell surface antigens: The cells are incubated with an antibody against the cell surface antigen of interest, and then reacted with a second antibody which is conjugated to a fluorescent dye. The cells are then evaluated using a fluorescence activated cell sorter to determine whether they are fluorescent and therefore possess the cell surface antigen.

(13) Cell-cell hybrid studies for identification of tumor suppressor activity (Stanbridge, et al., *Science*, 215:252–259, 1982). To determine whether these cell lines contain tumor suppressor genes, they are fused to malignant tumor cells. The presence of tumor suppressor genes is indicated by loss of malignancy e.g., as detected by loss of ability to form tumors in athymic nude mice, in the hybrid cells.

(14) Identification of novel genes including transforming genes in naturally occurring cancers described in paragraph 6 above, growth factor genes as described in paragraph 9 above, tumor suppressor genes as described in paragraph 13 above, using standard molecular biological techniques (Davis, et al., *Methods in Molecular Biology*, New York: Elsevier., 1986) and techniques such as cDNA subtraction cloning and the like.

Of course, a kit for screening carcinogenic or antineoplastic agents and for any other usage as described herein supra, is easily assembled, comprising container(s) containing the cell line(s) of the present invention. Other components routinely found in such kits can also be included with instructions for performing the test.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A substantially pure cell line of immortalized non-tumorigenic, human bronchial epithelial cells, said cells transformed with a gene encoding the large T-antigen of Simian Virus 40 and said cell line originating from individual cells that remain living in a cell culture of non-immortal bronchial epithelial cells transformed with a gene encoding the large T-antigen of Simian Virus 40 wherein the cell culture has undergone crisis.

2. The cell line of claim 1 having the identifying characteristics of BET-2A (ATCC CRL 9443).

3. A human bronchial epithelial cell line which has been rendered tumorigenic by transfection of the cells according to claim 1 with an oncogene, said cell line being selected from the group consisting of those having the identifying characteristics of ATCC CRL 9871, 9866, 9870, 9867, 9869, 9864, 9868, 9483, BERB (ATCC CRL 10635) and BERB (subclone 2) (ATCC CRL 10634).

4. The cell line of claim 3 having the identifying characteristics of ATCC CRL 9871.

5. The cell line of claim 3 having the identifying characteristics of ATCC CRL 9866.

6. The cell line of claim 3 having the identifying characteristics of ATCC CRL 9870.

7. The cell line of claim 3 having the identifying characteristics of ATCC CRL 9867.

8. The cell line of claim 3 having the identifying characteristics of ATCC CRL 9869.

9. The cell line of claim 3 having the identifying characteristics of ATCC CRL 9864.

10. The cell line of claim 3 having the identifying characteristics of ATCC CRL 9868.

11. The cell line of claim 3 having the identifying characteristics of ATCC CRL 9483.

12. The cell line of claim 3 having the identifying characteristics of BERB (ATCC CRL 10635).

13. The cell line of claim 3 having the identifying characteristics of BERB (subclone 2) (ATCC CRL 10634).

14. A kit for screening a carcinogenic agent comprising a container containing a substantially pure culture of immortalized non-tumorigenic human bronchial epithelial cells said cells transformed with a gene encoding the large T-antigen of Simian Virus 40 and said culture originating from individual cells that remain living in a cell culture of non-immortal bronchial epithelial cells transformed with a gene encoding the large T-antigen of Simian Virus 40 that has undergone crisis.

15. A kit of claim 14 wherein the cell line has the identifying characteristics of BET-2A (ATCC CRL 9443).

16. A kit for screening antineoplastic agents or chemotherapeutic agents comprising a container of cells selected from cell lines consisting of cells having the identifying characteristics of ATCC CRL 9871, 9866, 9870, 9867, 9869, 9864, 9868, 9865, 9483, BERB (ATCC CRL 10635) or BERB (subclone 2) (ATCC CRL 10634).

17. A method for testing carcinogenicity of an agent, comprising: (a) culturing a substantially pure culture of immortalized non-tumorigenic human bronchial epithelial cells, said cells transformed with the large T-antigen of Simian Virus 40 and said culture originating from individual cells that remain living in a cell culture of non-immortal bronchial epithelial cells transformed with a gene encoding the large T-antigen of Simian Virus 40 that has undergone crisis; (b) contacting said culture with an agent suspected of being carcinogenic; and (c) detecting the carcinogenic effect of the agent upon the culture.

18. A method of claim 17 wherein the cell culture has the identifying characteristics of BET-2A (ATCC CRL 9443).

19. A method for testing antineoplastic activity of an agent, comprising: (a) culturing cells having the identifying characteristics of ATCC CRL 9871, 9866, 9870, 9867, 9869, 9864, 9868, 9483, BERB (ATCC CRL 10635) or BERB (subclone 2) (ATCC 10634); (b) contacting said cells with a potential antineoplastic agent; and (c) determining growth of said cells, a lack of growth of said cells being indicative of antineoplastic potency of said agent.

* * * * *